United States Patent [19]

Ziegler et al.

[11] 4,186,143
[45] Jan. 29, 1980

[54] CHENODEOXYCHOLIC ACID RECOVERY PROCESS

[75] Inventors: Peter Ziegler, Toronto; Michael C. Attwell, Islington; Thomas F. Massiah, Agincourt; Roberto A. Vergottini, Bramalea, all of Canada

[73] Assignee: Canada Packers Limited, Toronto, Canada

[21] Appl. No.: 932,176

[22] Filed: Aug. 9, 1978

Related U.S. Application Data

[63] Continuation of Ser. No. 808,082, Jun. 20, 1977, abandoned, which is a continuation-in-part of Ser. No. 696,425, Jun. 15, 1976, abandoned.

[51] Int. Cl.$^2$ .............................................. C07J 9/00
[52] U.S. Cl. ................................................... 260/397.1
[58] Field of Search ..................................... 260/397.1

[56] References Cited

U.S. PATENT DOCUMENTS

| | | | |
|---|---|---|---|
| 3,919,266 | 11/1975 | Saltzman | 260/397.1 |
| 3,965,131 | 6/1976 | Wiele et al. | 260/397.1 |
| 4,014,908 | 3/1977 | Saltzman | 260/397.1 |
| 4,022,806 | 5/1977 | Frost et al. | 260/397.1 |

*Primary Examiner*—Elbert L. Roberts
*Attorney, Agent, or Firm*—Ridout & Maybee

[57] ABSTRACT

A method of isolating chenodeoxycholic acid from hog bile is provided, which comprises the steps of treating the hog bile under saponifying conditions separating the bile acids from the water-soluble constituents of the saponified bile; esterifying the bile acids to obtain a mixture of bile acid esters; isolating from the mixture of bile acid esters the hyodeoxycholic acid ester as its adduct with a compound selected from the group consisting of benzene and toluene; treating the remaining bile acid esters under acetylating conditions; isolating the hyocholic acid ester triacetate; isolating the chenodeoxycholic acid ester diacetate; treating the chenodeoxycholic acid ester diacetate under saponifying conditions; isolating the chenodeoxycholic acid thus obtained; and, optionally purifying the chenodeoxycholic acid.

The method described yields chenodeoxycholic acid of exceedingly high purity, which may be used in the treatment of gallstones by their dissolution in vivo.

29 Claims, No Drawings

CHENODEOXYCHOLIC ACID RECOVERY PROCESS

This is a continuation of application Ser. No. 808,082 filed June 20, 1977, which application is a continuation-in-part of application Ser. No. 696,425 filed June 15, 1976, both now abandoned.

This invention relates to chenodeoxycholic acid, and more particularly to a process for the isolation of chenodeoxycholic acid from hog bile.

Chenodeoxycholic acid, or $3\alpha, 7\alpha$-dihydroxy-$5\beta$-cholanic acid, is one of the bile acids found in the bile of oxen, pigs, guinea pigs, bears, hens, geese and other fowl, and man. Isolation of chenodeoxycholic acid from goose bile was first reported by Windhaus et al, Z. Physiol. Chem. 140, 177–185 (1924). Although processes for the isolation of chenodeoxycholic acid are well-known, these processes have been laboratory processes of academic interest only, and have not been satisfactory for large-scale commercial usage, particularly as the reported yields have been low. As a consequence, chenodeoxycholic acid is most commonly obtained by synthesis from cholic acid, which in turn may be isolated from beef bile. (See, for example, Fieser & Rajagopalan, J. Am. Chem. Soc. 72, 5530 (1950)).

Until very recently, chenodeoxycholic acid had remained only a laboratory curiosity. In the early 1970's, it was discovered that the acid had the surprising ability to dissolve gall stones in vivo. See, for example, DISSOLUTION OF CHOLESTEROL GALLSTONES BY CHENODEOXYCHOLIC ACID, DANZINGER R. G., et al, New England Journal of Medicine 286, 1 (1972). It then became important to develop reliable processes for the large-scale manufacture of chenodeoxycholic acid, which yielded a product sufficiently pure to be used as a medicine.

The most commonly used source from which chenodeoxycholic acid has been isolated, according to the previous reports, is goose bile. However, goose bile is not available in sufficient quantities to permit economical commercial manufacture of the chenodeoxycholic acid, and, even if it were, the small amounts of bile obtained from each goose gall bladder would make the collection of sufficient quantities of the bile impractical.

A heretofore little-used source of chenodeoxycholic acid is hog bile, which now has been found to be a source of chenodeoxycholic acid suitable for use in large-scale commercial production of this bile acid, as it is readily and easily available, and has few other useful applications.

Hog bile is a much more complex mixture than the bile of other animals, containing appreciable quantities of four bile acids, while cattle, poultry and human bile contain appreciable quantities of two bile acids only. The four bile acids found in hog bile are chenodeoxycholic acid, hyodeoxycholic ($3\alpha, 6\alpha$-dihydroxy-$5\beta$-cholanic) acid, hyocholic ($3\alpha, 6\alpha, 7\alpha$-trihydroxy-$5\beta$-cholanic) acid, and $3\alpha$-hydroxy-6-oxo-$5\alpha$-cholanic acid.

Because of the complex nature of hog bile, the isolation of the individual bile acids is much more difficult than the isolation of one component of, e.g. beef bile, particularly if the components must be isolated efficiently, and with the high degree of purity necessary to permit its use as a medicine.

Accordingly, it is an object of the present invention to provide an improved method of isolating and purifying chenodeoxycholic acid from hog bile.

It has been found that chenodeoxycholic acid may be isolated from hog bile using the commercially-adaptable process described below. The chenodeoxycholic acid isolated by the process of this invention is of exceedingly high purity and is readily acceptable as a medicinal agent for the treatment of gallstones.

According to the present invention, there is provided a process for isolating and purifying chenodeoxycholic acid from hog bile which comprises the steps of:

1. treating said hog bile under saponifying conditions;
2. separating the bile acids from the water-soluble constituents of the saponified bile;
3. esterifying said bile acids to obtain a mixture of bile acid esters;
4. isolating from said mixture of bile acid esters the hyodeoxycholic acid ester;
5. treating the remaining bile acid esters under acetylating conditions;
6. isolating the hyocholic acid ester triacetate;
7. isolating the chenodeoxycholic acid ester diacetate;
8. treating said chenodeoxycholic acid ester diacetate under saponifying conditions; and
9. isolating the chenodeoxycholic acid thus obtained.

According to a preferred embodiment of the present invention, there is provided a process for the isolation and purification of chenodeoxycholic acid from hog bile which comprises the steps of:

1. treating the bile under saponifying conditions by refluxing the bile in the presence of an aqueous solution of suitable base;
2. acidifying the saponified bile with a suitable acid while extracting the bile acids therefrom with an essentially water-immiscible organic solvent having low solubility in the saponified and acidified bile and exerting a preferential solvent action towards the bile acids therein as compared with the remaining constituents of said bile, separating the resulting aqueous and solvent phases and separating the bile acids from the solvent phase;
3. reacting the bile acids with a suitable alcohol in the presence of a suitable acid catalyst;
4. neutralizing the reaction mixture thus obtained with a suitable base;
5. isolating the esterified bile acids thus obtained;
6. dissolving the bile acid esters in a suitable solvent comprising a compound selected from the group consisting of benzene and toluene;
7. treating the solution thus obtained to precipitate therefrom solid matter having a high content of an adduct of hyodeoxycholic acid ester with a compound selected from the group consisting of benzene and toluene;
8. separating the solution so treated into a substantially solid portion and a substantially liquid portion;
9. separating the solvent from the substantially liquid portion to obtain a substantially dry mixture of the remaining esterified bile acids;
10. reacting the remaining bile acid esters with acetic anhydride and a substance selected from the group consisting of sodium acetate and pyridine;
11. separating excess acetic anhydride from the reaction mixture thus obtained to obtain a substantially dry residue;
12. dissolving said residue, having a high content of acetylated bile acid esters, in a suitable solvent;
13. treating the solution thus obtained to precipitate therefrom a solid having a high content of acetylated hyocholic acid ester;

14. separating the solution so treated into a substantially solid portion and a substantially liquid portion;
15. separating the solvent from the substantially liquid portion, to obtain a substantially dry solid matter;
16. dissolving the substantially dry solid matter, having a high content of the remaining acetylated bile acid esters, in a suitable solvent;
17. treating the solution thus obtained to precipitate therefrom a solid having a high content of chenodeoxycholic acid ester diacetate;
18. separating the solution so treated into a substantially solid portion and a substantially liquid portion;
19. redissolving the substantially solid portion in a suitable solvent;
20. treating the solution thus obtained to precipitate therefrom a solid having a high content of chenodeoxycholic acid ester diacetate;
21. separating the solution so treated into a substantially solid portion and a substantially liquid portion;
22. treating the substantially solid portion under saponifying conditions in an aqueous medium by refluxing with a suitable base;
23. acidifying the saponified material with a suitable acid while extracting with an essentially water-immiscible organic solvent exerting a preferential solvent action toward the chenodeoxycholic acid contained in said saponified and acidified material as compared with said remaining constituents of said saponified and acidified material and separating the resulting solvent and aqueous phases;
24. treating the solvent phase, containing the chenodeoxycholic acid, by concentrating and cooling until solid matter containing a high content of chenodeoxycholic acid is precipitated therefrom;
25. separating the solution so treated into a substantially liquid portion and a substantially solid portion; and
26. treating the substantially solid portion by drying.

The hog bile to be used in this process may be fresh or inspissated, and may be whole or defatted. The bile may be defatted before or after the saponification of the bile.

The saponification of bile has been described in Canadian Pat. No. 533,769, issued on Nov. 27, 1965 to Canada Packers Limited. If fresh bile is used, no preliminary treatment of this bile is necessary. If inspissated bile is used, it may be diluted so that its total solids content approximates that of fresh bile (10%–14%). The bile is saponified by refluxing it with 5% to 20% of a suitable base, such as potassium hydroxide or sodium hydroxide, for between 16 and 24 hours, although the reflux time may vary, depending on the pressure used, and on the concentration of the base. Normally the saponification is carried out at or slightly above atmospheric pressure. The saponified mixture is then brought to about pH 8 with a suitable mineral acid, such as hydrochloric acid or sulphuric acid, which is usually added in a concentrated form in order to increase the water content as little as possible.

If desired, the 3α-hydroxy-6-oxo-5α-cholanic acid may be isolated as its salt before extraction of the remaining bile acids from the saponified bile. This isolation is accomplished by crystallization of the crude salt from the saponified bile after the bile has been diluted to about 2–3 times its original volume with cold water and held at a temperature of 5°–20° C. for a period of 16–24 hours. The removal of the 3α-hydroxy-6-oxo-5α-cholanic acid at this point may improve the yield of chenodeoxycholic acid in the process without substantially affecting the remainder of the process.

It is generally preferred to separate the bile acids from the neutralized saponified bile by solvent extraction. If this procedure is followed, a bleaching agent, such as sodium hydrosulfite, and an organic solvent, which must have a low solubility in water and in the acidified bile and in which the bile acids have a high solubility, is added while maintaining the saponified bile at an elevated temperature. After the solvent and bleaching agent have been added, the saponified bile is acidified to approximately pH 5 by the addition of a suitable mineral acid.

Suitable organic solvents are ethyl acetate, methyl isobutylketone, n-hexanol, toluene, and halogenated hydrocarbons such as ethylene dichloride. A preferred solvent is ethyl acetate, and with this preferred solvent, a temperature range of 50° to 55° has been found to be most satisfactory.

The addition of the mineral acid and the solvent causes the mixture of saponified and acidified bile and solvent to separate into an aqueous phase and an organic phase. The addition of the small amount of bleaching agent lightens the aqueous phase, and aids in the subsequent visual separation of aqueous and solvent layers, as it does not have any appreciable decolourizing effect on the solvent solution of bile acids. Approximately 0.5% of the bleaching agent, such as sodium hydrosulfite, based on the weight of the starting bile has been found adequate for this purpose.

The aqueous and organic layers are separated, and the aqueous and interface layers, containing the water-soluble organic impurities, the inorganic compounds, and the insoluble materials are rejected. The organic phase may then be treated with a decolourizing agent such as bleaching earth and charcoal followed by filtration of the organic phase and by washing of the filtered solids with a fresh amount of solvent.

The filtrate and washings are then combined and evaporated to dryness; a residue containing a high content of bile acids is obtained.

As an alternative to the solvent extraction process, the saponified and acidified bile may be treated with a suitable mineral acid until a solid containing a high content of bile acids is precipitated. This solid is removed from the solution by filtration, and is then further treated by azeotropic or oven drying. However, the solvent extraction procedure is preferred to this latter process, as the precipitated bile acids are often gummy and very difficult to separate satisfactorily by filtration.

Following the separation of the bile acids, the next step in the process is the esterification of these acids. The esterification is achieved by the reaction of the bile acids with a suitable alcohol, using a suitable acid catalyst. It is preferred to use the lower aliphatic alcohols for esterification, and in particular, methanol is preferred. As an acid catalyst, it is preferred to use sulphuric acid or hydrochloric acid, but p-toluenesulphonic acid may also be used.

The esterification is achieved by dissolving the residue obtained from the saponification step in the alcohol, and adding the necessary amount of the acid catalyst. The solution thus obtained is stirred at approximately room temperature for several hours. The reaction mixture is then neutralized to about pH 7, using a suitable base. Among the bases which may be used are sodium bicarbonate, sodium carbonate, sodium hydroxide, and suitable organic bases such as triethylamine. The solution may then be filtered to remove any inorganic salts present which may have been precipitated by the neutralization. The filtrate is then evaporated to dryness, separating the esterified bile acids from the remaining alcohol. A dry residue is obtained.

The hyodeoxycholic acid ester is then isolated from the other bile acid esters as follows. The residue remaining after the esterification step is dissolved in a suitable solvent, which comprises a compound, such as benzene or toluene, which forms an adduct or complex with the hyodeoxycholic acid ester. It is preferred to use benzene, as benzene can act both as the solvent and as the complexing agent. In order to assist the dissolution of the residue, the solvent is usually heated to about 60°-70° C. The volume of the solvent used is based on the weight of the total bile acids at the start of the process; about 1 to 4 liters of solvent per kilogram of bile acids are used.

The solution thus obtained is concentrated by evaporating some of the solvent, to about 40% to 60% of its original volume, and is then cooled, and preferably held at a temperature of 5°-15° C. for 10-24 hours. A thick slurry is obtained which is then filtered. The filter cake obtained is washed with the solvent used, and the washings are combined with the filtrate. The combined filtrate and washings are then evaporated to dryness. The solid separated by filtration may be dried, and consists primarily of the complex or adduct of the ester of hyodeoxycholic acid.

According to a preferred embodiment of the present invention, the bile acids are esterified with methanol, using sulphuric or hydrochloric acid as the catalyst. The methyl esters of the bile acids are thus obtained. The preferred solvent for the isolation of the methyl hyodeoxycholate is benzene, and the ester is isolated as the benzene adduct of methyl hyodeoxycholate.

Following the isolation of the hyodeoxycholic acid ester, the remaining bile acid esters are acetylated by any one of a number of known methods. For example, the solid residue obtained upon evaporation of the solvent is dissolved in acetic anhydride, and sodium acetate or pyridine is added to the solution, which is then refluxed for between 3 and 10 hours, preferably 5 hours.

The solution is then treated to remove any excess acetic anhydride by, for example, evaporation. The addition of a suitable alcohol, such as methanol, to the residue to form an acetate with the anhydride, or the addition of a solvent such as toluene to the residue, assists in the removal of this excess upon distillation.

Alternatively, the acetylated bile acid esters may be separated by crystallization from the acetic anhydride. The solution after refluxing is slightly concentrated, and then held at a temperature of about 5° C. for a period of 10-20 hours. The slurry thus obtained is filtered, the filter cake is washed with fresh acetic anhydride, and the filtrate and washings combined. The acetic anhydride is separated from the filtered solution by, for example, evaporation, the separation being assisted by the addition of a suitable alcohol or toluene as described above. If desired or necessary, the residue remaining after the distillation may be redissolved in the solvent, and redistilled.

Following the isolation of the acetylated bile acid esters, the hyocholic acid ester is separated as its triacetate. The residue from either of the alternative processes described above is dissolved in a suitable solvent, preferably a non-polar solvent comprising n-heptane, hexane, n-octane, iso-octane, n-pentane, cyclohexane, cyclopentane, or cyclopentene, more preferably n-heptane, hexane or n-octane. The hyocholic acid ester triacetate is separated from the solution thus obtained by crystallization, at a temperature between 15° C. and 30° C., preferably 20° C. The volume of solvent used is not critical, but is preferably 2-4 liters per kilogram of bile acid ester acetates present. The temperature range is, however, more critical. At temperatures higher than 30° C., more of the hyocholic acid ester triacetate stays in solution, and contaminates the product later, whereas at temperatues lower than 15° C., the chenodeoxycholic acid ester diacetate co-crystallizes with the hyocholic acid ester triacetate, making recovery more difficult.

As an alternative to the above crystallization process, it has been found that in some instances a higher yield may be obtained by a first crystallization at a low temperature, preferably about 5° C., followed by a warming of the solution and precipitate to redissolve any of the chenodeoxycholic acid ester diacetate which has precipitated at the low temperature, and then completing the crystallization of the hyocholic acid ester triacetate at 20°-25° C.

Following the crystallization of the hyocholic acid ester triacetate, the solution is filtered, and the filter cake is washed with a suitable solvent, such as hexane. The washed filter cake is then dried, and consists of a solid having a high content of hyocholic acid ester triacetate. The filtrate and washings are combined and evaporated to dryness.

According to a preferred embodiment of the present invention, wherein methanol is used to esterify the bile acids, the precipitated and separated solid has a high content of methyl hyocholate triacetate.

The chenodeoxycholic acid ester diacetate is then isolated. The residue remaining after the filtrate and washings have been evaporated to dryness is dissolved in a suitable solvent, preferably a polar solvent, more preferably methanol, ethanol or isopropanol, and most preferably ethanol. The solvent may be heated to assist the dissolution of the residue. The volume of solution used is preferably 0.5 to 2.0 liters per kilogram of bile acid ester acetates.

The solution thus obtained is cooled, preferably held at a temperature of 0°-10° C. for a period of 16-48 hours, and then filtered. The filtrate is preserved, and the solid thus separated having a high content of chenodeoxycholic acid ester diacetate is washed with a suitable solvent, for example, ethanol, and then dried.

The dried solid is then redissolved in a suitable solvent, such as methanol, ethanol, isopropanol, and hexane, preferably ethanol or methanol, and then recrystallized from this solvent. The volume of solvent used in the recrystallization is preferably 2-6 liters per kilogram of chenodeoxycholic acid ester diacetate.

(The filtrate from the first crystallization may be discarded, or may be added to subsequent batches of hog bile to recover some of the chenodeoxycholic acid from the filtrate. Alternatively, several batches of filtrate may be collected, and treated in the same manner as the hog bile would be treated in order to recover the chenodeoxycholic acid ester diacetate therefrom).

The recrystallized chenodeoxycholic acid ester diacetate is then added to an aqueous solution of a suitable base, and refluxed for 8-18 hours, preferably 14 hours, to hydrolyze the ester groups. Suitable bases include sodium hydroxide and potassium hydroxide. The solution is then diluted with water, and acidified with a suitable mineral acid to about pH 4.5.

The chenodeoxycholic acid is then extracted by any one of a number of different but known techniques. For example, a suitable, essentially water-immiscible solvent such as ethyl acetate, methylisobutylketone, ethylene dichloride, n-butyl acetate, preferably ethyl acetate, is added to the diluted and acidified saponification mixture, and agitated thoroughly. The mixture separates into an aqueous and an organic phase, which phases are then separated, and the aqueous phase discarded. The organic phase is washed with, for example, a 10% sodium chloride solution, and then is partially evaporated to concentrate the solution. The solution is cooled until precipitation occurs, and the solution is diluted with a diluent in which chenodeoxycholic acid is insoluble, preferably hexane or cyclohexane. The diluted slurry is then refrigerated for a period of 10-20 hours, and then filtered, with the solids being retained and washed with fresh solvent or mixture of solvents. The washed solid is then dried, yielding essentially pure chenodeoxycholic acid.

The following examples are illustrative of the process of the present invention and are not intended to limit the scope thereof.

EXAMPLE 1

Sodium hydroxide (100 g) was added to fresh hog bile (1 liter) and the mixture was refluxed for 24 hours. The solution was cooled to room temperature and adjusted to pH 8 with concentrated sulphuric acid. Sodium hydrosulphite (5.3 g) was added and the mixture was stirred for 15 min. After the addition of ethyl acetate (450 ml), the pH of the mixture was adjusted to pH 5 with dilute sulphuric acid. The mixture was stirred for 30 min. and then allowed to separate. The lower aqueous layer was drained and discarded. Filtrol TM (10 g) and charcoal (10 g) were added to the upper organic phase. The mixture was stirred for 30 min., filtered, and the filter cake washed with ethyl acetate (50 ml). The filtrate and washings were evaporated to dryness.

The residue was dissolved in methanol (300 ml), concentrated sulphuric acid (4.0 ml; 98%) was added and the solution was stirred at room temperature overnight. After neutralization (to ca pH 7) with solid sodium bicarbonate (ca 28 g), the mixture was filtered and then evaporated to dryness under vacuum. The residue was dissolved in hot benzene (320 ml). The solution was concentrated to about 225 ml, and refrigerated overnight. The slurry was filtered, and the filter cake (methyl hyodeoxycholate-benzene adduct) was washed with benzene.

The benzene filtrate and washings were evaporated to dryness. Acetic anhydride (75 ml) and anhydrous sodium acetate (7.5 g) were added to the residue and the mixture was refluxed for 5 hours. A portion of the solvent (25 ml) was distilled and the residual slurry was refrigerated overnight. The mixture was filtered, and the filter cake washed with cold acetic anhydride (30 ml).

The filtrate and washings were evaporated to dryness in vacuo. Residual acetic anhydride was removed by the addition and distillation of toluene (2×30 ml). The residue was dissolved in hexane (200 ml) and the solution was refrigerated overnight. The mixture was heated to reflux, refluxed for 10 min., cooled to room temperature and stirred at room temperature for 3 hours. The slurry was filtered, and the filter cake was washed with hexane.

The filtrate was evaporated to dryness in vacuo. The residue was dissolved in hot ethanol (46 ml). The solution was cooled and refrigerated overnight. The slurry was filtered. The filter cake was washed with ethanol (27 ml at 5° C.), and dried in vacuo at 50°-60° C. The crude methyl chenodeoxycholate diacetate weighed 19.95 g. This was recrystallized from 4 volumes of ethanol which gave 17.4 g product: mp 112°-114° C. (softens 110° C.); $[\alpha]_D^{25}+10.5°$ (c=1, dioxane); $[\alpha]_D^{25}+15.4°$ (c=1, $CHCl_3$).

The methyl chenodeoxycholate diacetate (17.4 g) was added to a solution of sodium hydroxide (17 g) in water (170 ml). After refluxing the mixture for 14 hours, the solution was diluted with water (350 ml), and adjusted to pH 4.5 with sulphuric acid. The mixture was extracted with ethyl acetate (225 ml). The ethyl acetate extract was washed with 10% aqueous sodium chloride (50 ml) and then evaporated to about 70 ml. The solution was cooled and hexane (70 ml) was added. The mixture was refrigerated overnight and then filtered. The filter cake was washed with ethyl acetate-hexane (40 ml; 1/1) and dried in vacuo at 60° C. The chenodeoxycholic acid weighed 11.5 g: mp 141°-144° C.; $[\alpha]_D^{25}+10.5°$ (c=1, dioxane); $[\alpha]_D^{25}+11.2°$ (c=2, ethanol).

EXAMPLE 2

Inspissated hog bile (334 g) was dissolved in hot water (1700 ml) and saponified with sodium hydroxide (200 g) as in example 1. The hydrolyzate was worked up as in example 1 but using twice the amount of reagents.

After recrystallization the yield of methyl chenodeoxycholate diacetate was 32.5 g [m.p. 113°-115° C.; $[\alpha]_D^{25}+14.5°$ (c=1, $CHCl_3$)] which yielded 21.3 g chenodeoxycholic acid. m.p. 139°-142° C.; $[\alpha]_D^{25}+10.0°$ (c=2, ethanol); $[\alpha]_D^{25}+9.5°$ (c=1, dioxane).

EXAMPLE 3

A process was carried out according to example 1 except that the crystallization from acetic anhydride after the acetylation was omitted, methanol instead of toluene was used to remove residual acetic anhydride, and the hexane crystallization was carried out at room temperature (24° C.) for 3 hours. The yield of methyl chenodeoxycholate diacetate was 15.5 g: m.p. 113°-115° C.; $[\alpha]_D^{25}+13.5°$ (c=1, $CHCl_3$).

EXAMPLE 4

A process was carried out according to example 1 except that toluene was used in place of benzene for separation of the methyl hyodeoxycholate as an adduct with toluene. The methyl chenodeoxycholate diacetate [17.1 g m.p. 112°-115° C.; $[\alpha]_D^{25}+18.5°$ (c=1, $CHCl_3$)] yielded 10.7 g somewhat impure chenodeoxycholic acid: m.p. 148°-165° C.; $[\alpha]_D^{25}+9°$ (c=1, dioxane); $[\alpha]_D^{25}+6.7°$ (c=2, ethanol).

EXAMPLE 5

Fresh hog bile (330 ml) was processed as in example 1 except that methyl isobutyl ketone (200 ml) instead of ethyl acetate was used for extraction of the bile acids after saponification of the bile. The yield of methyl chenodeoxycholate diacetate was 3.5 g: m.p. 116°-119° C.; $[\alpha]_D^{25}+13.2°$ (c=1, $CHCl_3$).

EXAMPLE 6

Methyl chenodeoxycholate diacetate (15 g) obtained as in example 2 was saponified as in example 2 except that methyl isobutyl ketone was used for extraction in place of ethyl acetate, and the chenodeoxycholic acid was crystallized from a mixture of methyl isobutyl ketone and hexane. The chenodeoxycholic acid weighed 9.2 g: m.p. 141°–144° C.; $[\alpha]_D^{23}+13.1°$ (c=1, CHCl$_3$); $[\alpha]_D^{23}+9.9°$ (c=1, dioxane).

EXAMPLE 7

Inspissated hog bile (30 g) was processed as in example 2 except that n-hexanol was used in place of ethyl acetate for extraction of the bile acids after saponification of the bile. The recovery of methyl chenodeoxycholate diacetate was 2.2 g: m.p. 112°–114° C.; $[\alpha]_D^{25}+16.5°$ (c=1, CHCl$_3$).

EXAMPLE 8

Hog bile (500 ml) was saponified as in example 1. The hydrolyzate was cooled to 10° C., filter-aid (12 g) added, and the mixture neutralized to pH 4.5 with sulphuric acid. The precipitated crude bile acids were filtered, added to benzene (400 ml) and azeotropically dried by distillation of the benzene. When the system was dry, the residual benzene was distilled. The residue was esterified and worked up as in Example 3. The recrystallized methyl chenodeoxycholate diacetate [8.5 g; m.p. 110°–111° C.; $[\alpha]_D^{25}+14.2°$ (c=1, CHCl$_3$)] was processed as in Example 1 to chenodeoxycholic acid [5.8 g; m.p. 141°–144° C.; $[\alpha]_D^{25}+15.6°$ (c=1, CHCl$_3$)].

EXAMPLE 9

Hog bile (500 ml) was saponified as in Example 1. Toluene (500 ml) was added to the partially cooled (about 85° C.) hydrolyzate and the mixture neutralized to pH 4.5 with sulphuric acid keeping the temperature at 80°–85° C. On standing the mixture separated into 3 layers. The lower aqueous layer was discarded. The upper 2 layers (oil and toluene) were azeotropically dried by distillation of the toluene using a Dean-Stark trap. When dry, the solvent was distilled and the residue esterified and worked up as in Example 3. The recrystallized methyl chenodeoxycholate diacetate [7.2 g; m.p. 111°–112° C.; $[\alpha]_D^{25}+13.8°$ (c=1, CHCl$_3$)] was processed as in Example 1 to chenodeoxycholic acid [4.9 g; m.p. 143°–146° C.; $[\alpha]_D^{25}+13.6°$ (c=1, CHCl$_3$)].

EXAMPLE 10

Inspissated hog bile (560 g) was dissolved in hot water (3.21). Sodium hydroxide (400 g) was added, the solution refluxed for 22 hours, and then cooled to 15° C. Filter-aid (100 g e.g. Hyflo Super-cel) was added and the mixture was acidified to pH 2 with sulphuric acid keeping the temperature at 10°–15° C. The mixture was filtered. The filter cake was washed with water and dried in a vacuum oven at 45°–50° C. The dry crude bile acid mixture weighed 510 g. A portion (128 g) of the solid was extracted with warm acetone (400 ml). The solution was charcoaled and then refrigerated at 5° C. overnight. The crystals were filtered. The filtrate was evaporated to dryness, and the residue esterified, acetylated, and processed as in Example 1. The methyl chenodeoxycholate diacetate [15.4 g; m.p. 109°–110° C.; $[\alpha]_D^{24}+12.7°$ (c=1, CHCl$_3$)] yielded 10.2 g chenodeoxycholic acid: m.p. 141°–144° C.; $[\alpha]_D^{23}+12.5°$ (c=1, CHCl$_3$); $[\alpha]_D^{23}+9.7°$ (c=1, dioxane).

EXAMPLE 11

Inspissated hog bile (150 g containing ca 110 g solids; equivalent to 1 liter of fresh bile) was dissolved in hot water (1000 ml). Sodium hydroxide (100 g) was added, and the mixture was refluxed for 20 hours. The solution was cooled to about 25° C., cold tap water (1500 ml) was added, and the solution was refrigerated overnight. Filter-aid (10 g) was added and the slurry was filtered to remove the precipitated crude sodium 3α-hydroxy-6-ketocholanate.

The filtrate was adjusted to pH 8 with concentrated sulphuric acid. Sodium hydrosulphite (5 g) was added and the solution was stirred for 15 minutes. After the addition of ethyl acetate (400 ml), the pH of the mixture was adjusted to pH 5 with dilute sulphuric acid. The mixture was stirred for 30 minutes and then allowed to separate. The lower aqueous layer was drained and discarded. Filtrol TM (7 g) and charcoal (7 g) were added to the upper organic phase. The mixture was stirred for 30 min., filtered, and the filter cake washed with ethyl acetate (50 ml). The filtrate and washings were evaporated to dryness.

The residue was dissolved in methanol (300 ml), conc. sulphuric acid (4.0 ml) was added and the solution stirred at room temperature overnight. After neutralization (to ca pH 7) with sodium bicarbonate, the mixture was filtered and evaporated to dryness. The residue was dissolved in hot benzene (320 ml). The solution was concentrated to about 225 ml, and refrigerated overnight. The slurry was filtered, and the filter cake (methyl hyodeoxycholate benzene adduct) was washed with benzene.

The benzene filtrate and washings were evaporated to dryness. Acetic anhydride (75 ml) and anhydrous sodium acetate (7.5 g) were added to the residue, and the mixture was refluxed for 5 hours. The excess acetic anhydride was then distilled. Methanol (35 ml) was added to the residue, the mixture was refluxed for 15 minutes, and then evaporated to dryness to remove residual acetic anhydride.

The residue was dissolved in hexane (200 ml) at reflux, and the solution was stirred at 20° C. overnight. The slurry was filtered and the filter cake (crude methyl hyocholate triacetate) was washed with hexane.

The filtrate was evaporated to dryness. The residue was dissolved in hot ethanol (46 ml) and the solution was refrigerated overnight. The slurry was filtered. The filter cake was washed with cold ethanol (27 ml) and dried in vacuo at 60° C. The crude methyl chenodeoxycholate diacetate (21.5 g) was recrystallized from 3 volumes of ethanol which gave 18.5 g product: m.p. 119°–121° C. (softening 110° C.); $[\alpha]_D^{25}+10.4°$ (c=1, dioxane); $[\alpha]_D^{25}+13.8°$ (c=1, CHCl$_3$).

The methyl chenodeoxycholate diacetate (18.5 g) was added to a solution of sodium hydroxide (18.5 g) in water (185 ml). After refluxing for 14 hours, the solution was neutralized to pH 4.5 with sulphuric acid and was extracted with ethyl acetate. The aqueous layer was discarded. The ethyl acetate extract was washed with 6% aqueous sodium chloride followed by water, and then, it was evaporated to about 90 ml. The solution was cooled and hexane (90 ml) was added. After overnight refrigeration, the slurry was filtered. The filter cake was washed with hexane (20 ml) and dried in vacuo at 60° C. The product, chenodeoxycholic acid, weighed 12.7 g: m.p. 142°–5° C.; $[\alpha]_D^{25}+13.0°$ (c=1, CHCl$_3$).

What we claim as our Invention is:

1. A process for the isolation and purification of chenodeoxycholic acid from hog bile which comprises the steps of:

(a) saponifying the bile by refluxing the bile in the presence of an aqueous solution of a suitable base;

(b) adjusting the pH of the saponified bile to about pH 8 by adding a mineral acid thereto;

(c) admixing said bile with an essentially water-immiscible solvent having low solubility in said bile and at an acidic pH exerting a preferential solvent action towards the bile acids therein as compared with the remaining constituents of said bile thus forming a two-phase mixture comprising an aqueous and an organic phase and subsequently acidifying said aqueous phase to about pH 5 by adding a diluted mineral acid thereto, separating the organic and aqueous phases and recovering a mixture of bile acids from the organic phase;

(d) esterifying the bile acids by reaction with a suitable alcohol in the presence of a suitable acid catalyst;

(e) neutralizing the reaction mixture thus obtained;

(f) recovering a mixture of bile acid esters from said reaction mixture;

(g) removing substantially all of the hyodeoxycholic acid ester from the remainder of said esterified bile acids by dissolving said mixture of bile acid esters in a suitable solvent comprising a complexing agent selected from the group consisting of benzene and toluene;

(h) treating the solution thus obtained to separate therefrom solid matter having a high content of an adduct of the complexing agent and the hyodeoxycholic acid ester;

(i) recovering from the remaining solution a substantially dry mixture of the remaining bile acid esters;

(j) acetylating the remaining bile acid esters by reacting said mixture with acetic anhydride and a compound selected from the group consisting of sodium acetate and pyridine, and separating from the reaction mixture so obtained a substantially dry mixture of acetylated bile acid esters;

(k) removing substantially all of the acetylated hyocholic acid ester from said mixture of acetylated bile acid esters by dissolving said mixture in a suitable non-polar solvent and treating the solution thus obtained to precipitate therefrom a solid having a high content of acetylated hyocholic acid ester;

(l) treating the remaining solution by evaporation to obtain a residue comprising a substantially dry mixture of the remaining acetylated bile acid esters;

(m) isolating chenodeoxycholic acid ester diacetate from said residue by dissolving said residue in a suitable polar solvent, treating the solution thus obtained to precipitate therefrom a solid having a high content of chenodeoxycholic acid ester diacetate and separating said solid from said remaining solution;

(n) purifying said chenodeoxycholic acid ester diacetate by dissolving said solid in a suitable polar solvent and treating the solution thus obtained to recover therefrom substantially pure, dry chenodeoxycholic acid ester diacetate;

(o) saponifying said chenodeoxycholic acid ester diacetate by refluxing with an aqueous solution of a suitable base;

(p) acidifying the saponified solution to about pH 4.5 by the addition of a mineral acid;

(q) extracting the chenodeoxycholic acid by contacting said saponified and acidified solution with an essentially water-immiscible organic solvent which exerts preferential solvent action toward the chenodeoxycholic acid contained in said saponified and acidified material as compared with said remaining constituents of said saponified and acidified material thus forming a two phase mixture comprising an aqueous phase and an organic phase and separating the resulting organic and aqueous phases;

(r) isolating the chenodeoxycholic acid by treating said organic phase by concentrating and cooling until solid matter containing substantially pure chenodeoxycholic acid is precipitated therefrom, separating the organic phase so treated into a substantially liquid portion and substantially solid portion and treating the substantially solid portion by drying.

2. The process as defined in claim 1 wherein the base in step (a) is NaOH or KOH.

3. The process as defined in claim 2 wherein the base is present in an amount of 5 to 20% of the mixture.

4. The process as defined in claim 1 which, subsequent to step (a), further comprises the steps of diluting the saponified mixture to about 2–3 times its volume with water, allowing a crude salt of 3α-hydroxy-6-oxo-5α-cholanic acid to crystallize, and separating the crystallized crude salt from the diluted saponified mixture.

5. The process as defined in claim 1 wherein in step (c) the organic solvent is ethyl acetate.

6. The process as defined in claim 1 wherein in step (e) sodium bicarbonate is used to neutralize the reaction mixture.

7. The process as defined in claim 1 wherein step (f) comprises evaporating the neutralized solution to dryness.

8. The process as defined in claim 1 wherein in step (g) the solvent is benzene.

9. The process as defined in claim 1 wherein in step (g) the solvent is used in an amount of about 1 to 4 liters per kilogram of bile acids.

10. The process as defined in claim 1 wherein step (j) comprises dissolving the mixture of bile acid esters in acetic anhydride in the presence of pyridine or sodium acetate and heating at reflux temperature.

11. The process as defined in claim 1 wherein in step (j) the substantially dry mixture of acetylated bile acid esters is obtained by evaporating excess acetic anhydride from the reaction mixture.

12. The process as defined in claim 11 which further comprises the step of adding to the residue a solvent selected from the group of lower alkyl alcohols and toluol and reevaporating to dryness.

13. The process as defined in claim 11 wherein step (j) prior to evaporation comprises the steps of slightly concentrating the reaction-mixture, cooling the concentrated reaction-mixture to a temperature of about 5° C. for a period of about 10–20 hours, to precipitate a solid therefrom, and separating the solid so precipitated from the remaining reaction-mixture removing the solid from the slurry.

14. The process as defined in claim 1 wherein in step (k) the non-polar solvent is selected from the group consisting of n-heptane, hexane, n-octane, iso-octane, n-pentane, cyclohexane, cyclopentane, or cyclopentene.

15. The process as defined in claim 14, wherein the solvent is n-heptane, hexane, or n-octane.

16. The process as defined in claim 14, wherein the solvent is hexane.

17. The process as defined in claim 1, wherein in step (k) the solvent is used in an amount of from about 2-4 liters per kilogram of the crude mixture of acetylated bile acid esters.

18. The process as defined in claim 1, wherein in step (k) the solution is maintained at a temperature between 20° C. and 25° C. while said solid is precipitated therefrom.

19. The process as defined in claim 1, wherein in step (k) the treatment of the said solution further comprises the steps of maintaining said solution at a temperature of about 5° C. to form a slurry comprising a solid precipitate, re-warming the slurry to re-dissolve any chenodeoxycholic acid ester diacetate within the precipitate and maintaining the slurry at a temperature of between 20° C. and 25° C. to complete formation of the solid crystallisate.

20. The process as defined in claim 1 wherein in step (m) the solvent is an alcohol selected from the group consisting of methanol, ethanol and isopropanol.

21. The process as defined in claim 20, wherein the alcohol is ethanol.

22. The process as defined in claim 1 wherein in step (m) the solvent is used in an amount of about 0.5-2.0 liters per kilogram of residue.

23. The process as defined in claim 1 wherein in step (m) the treatment of the solution comprises cooling the solution to a temperature of about 0° C. to 10° C.

24. The process as defined in claim 23, wherein the solution is cooled and maintained at a temperature of about 0° C. to 10° C. for a period of about 16 to 48 hours.

25. The process as defined in claim 1, wherein in step (n) said chenodeoxycholic acid ester diacetate so recovered is re-crystallized from a solvent selected from the group consisting of methanol, ethanol, isopropanol, and hexane.

26. The process as defined in claim 25, wherein the solvent is methanol or ethanol.

27. The process as defined in claim 1, wherein in step (q) the water-immiscible organic solvent is selected from the group consisting of ethyl acetate, methyl isobutylketone, ethylene dichloride, and n-butyl acetate.

28. The process as defined in claim 27, wherein the solvent is ethyl acetate.

29. A process for the isolation and purification of chenodeoxycholic acid from hog bile which comprises the steps of:
 (a) saponifying the bile by refluxing the bile in the presence of an aqueous solution of a suitable base;
 (b) cooling the sponified mixture to a temperature of about 15° C.;
 (c) acidifying the cooled mixture to about pH 2 while maintaining it at a temperature of 10°–15° C.;
 (d) filtering the acidified mixture to obtain a filter-cake comprising a crude mixture of bile acids;
 (e) recrystallizing the crude mixture of bile acids from acetone;
 (f) esterifying the recrystallized mixture of bile acids by reaction with a suitable alcohol in the presence of a suitable acid catalyst;
 (g) neutralizing the reaction mixture thus obtained;
 (h) recovering a mixture of bile acid esters from said reaction mixture;
 (i) removing substantially all of the hyodeoxycholic acid ester from the remainder of said esterified bile acids by dissolving said mixture of bile acid esters in a suitable solvent comprising a complexing agent selected from the group consisting of benzene and toluene;
 (j) treating the solution thus obtained to separate therefrom solid matter having a high content of an adduct of the complexing agent and the hyodeoxycholic acid ester;
 (k) recovering from the remaining solution a substantially dry mixture of the remaining bile acid esters;
 (l) acetylating the remaining bile acid esters by reacting said mixture with acetic anhydride and a compound selected from the group consisting of sodium acetate and pyridine, and separating from the reaction mixture so obtained a substantially dry mixture of acetylated bile acid esters;
 (m) removing substantially all of the acetylated hyocholic acid ester from said mixture of acetylated bile acid esters by dissolving said mixture in a suitable non-polar solvent and treating the solution thus obtained to precipitate therefrom a solid having a high content of acetylated hyocholic acid ester;
 (n) treating the remaining solution by evaporation to obtain a residue comprising a substantially dry mixture of the remaining acetylated bile acid esters;
 (o) isolating chenodeoxycholic acid ester diacetate from said residue by dissolving said residue in a suitable polar solvent, treating the solution thus obtained to precipitate therefrom a solid having a high content of chenodeoxycholic acid ester diacetate and separating said solid from said remaining solution;
 (p) purifying said chenodeoxycholic acid ester diacetate by dissolving said solid in a suitable polar solvent and treating the solution thus obtained to recover therefrom substantially pure, dry chenodeoxycholic acid ester diacetate;
 (q) saponifying said chenodeoxycholic acid ester diacetate by refluxing with an aqueous solution of a suitable base;
 (r) acidifying the saponified solution to about pH 4.5 by the addition of a mineral acid;
 (s) extracting the chenodeoxycholic acid by contacting said saponified and acidified solution with an essentially water-immiscible organic solvent which exerts preferential solvent action toward the chenodeoxycholic acid contained in said saponified and acidified material as compared with said remaining constituents of said saponified and acidified material thus forming a two phase mixture comprising an aqueous phase and an organic phase and separating the resulting organic and aqueous phases;
 (t) isolating the chenodeoxycholic acid by treating said organic phase by concentrating and cooling until solid matter containing substantially pure chenodeoxycholic acid is precipitated therefrom, separating the organic phase so treated into a substantially liquid portion and substantially solid portion and treating the substantially solid portion by drying.

* * * * *